United States Patent [19]
Narayanan

[11] 3,969,392
[45] July 13, 1976

[54] TETRAHYDRO-CYCLOPROPA[B]NAPH-THALENES

[75] Inventor: Venkatachala L. Narayanan, Hightstown, N.J.

[73] Assignee: E. R. Squibb & Sons, Inc., Princeton, N.J.

[22] Filed: Sept. 15, 1975

[21] Appl. No.: 613,720

Related U.S. Application Data

[62] Division of Ser. No. 425,413, Dec. 17, 1973, Pat. No. 3,923,890, which is a division of Ser. No. 252,814, May 12, 1972, Pat. No. 3,796,760, which is a division of Ser. No. 73,668, Sept. 18, 1970, Pat. No. 3,694,512.

[52] U.S. Cl. .............................................. 260/473 F
[51] Int. Cl.² ........................................ C07C 69/76
[58] Field of Search ................................. 260/473 F

[56] References Cited
OTHER PUBLICATIONS

Chatterjee, A. et al., Chemical Abst., vol. 72, 78149m, (1970).
Swenton, J. S. et al., Chemical Abst., vol. 77, 61050c (1972).

*Primary Examiner*—Paul J. Killos
*Attorney, Agent, or Firm*—Lawrence S. Levinson; Merle J. Smith; Donald J. Barrack

[57] ABSTRACT

Compounds are provided having the structure

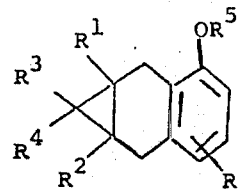

These compounds are useful as antiparasitic agents, antibacterial agents, and anti-inflammatory agents as well as surfact active agents.

1 Claim, No Drawings

TETRAHYDRO-CYCLOPROPA[B]NAPHTHALENES

This is a division of U.S. patent application Ser. No. 425,413, filed Dec. 17, 1973, now U.S. Pat. No. 3,923,890 which is a division of U.S. patent application Ser. No. 252,814, filed May 12, 1972, now U.S. Pat. No. 3,796,760, which is a division of U.S. patent application Ser. No. 73,668, filed September 18, 1970, now U.S. Pat. No. 3,694,512.

The present invention relates to tetrahydro-cyclopropanaphthalenes of the structure

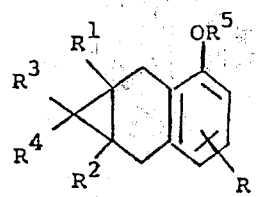

wherein R is hydrogen, lower alkyl, lower alkoxy, or cycloalkyl; $R^1$ and $R^2$ are the same or different and can be hydrogen, lower alkyl or lower alkoxy, $R^3$ and $R^4$ are the same or different and can be hydrogen, chlorine or bromine, although at least one of $R^3$ and $R^4$ is chlorine or bromine; $R^5$ is hydrogen, lower alkyl, aralkyl or $-(CH_2)_m CO_2R^6$ where $m = 1$ to 10, and $R^6$ is hydrogen, lower alkyl, or aralkyl. Furthermore, $R^5$ can be aminoalkyl having the structure $-(CH_2)_n-NR^7R^8$ wherein $n$ is 2 to 6, $R^7$ and $R^8$ can be the same or different and represent hydrogen, lower alkyl, aralkyl, monocyclic cycloalkyl, monocyclic aryl or hydroxy-lower alkyl and $R^7$ and $R^8$ can be taken together with the nitrogen to form a 5 to 7 membered monocyclic heterocyclic ring.

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like. The lower alkyl group can include substituents such as aryl.

The term "lower alkoxy" includes straight and branched chain lower alkyl groups attached to an oxygen.

The term "monocyclic aryl" as employed herein includes monocyclic carbocyclic aryl radicals, for instance, phenyl and substituted phenyl radicals, including lower alkyl phenyl, such as tolyl, ethylphenyl, butylphenyl and the like, di(lower alkyl)phenyl (e.g., dimethylphenyl, 3,5-diethylphenyl and the like), halophenyl (e.g., chlorophenyl, bromophenyl, and 2,4,6-trichlorophenyl) and nitrophenyl.

The term "monocyclic cycloalkyl" includes cyclic radicals containing from 3 to 6 ring members (e.g., cyclopropyl, cyclobutyl, cyclopentyl and cyclohexyl).

The radicals $-(CH_2)_m-$ and $-(CH_2)_n-$ encompass straight chain or branched bivalent lower alkyl groups.

Examples of the basic nitrogen containing radical symbolized by the group

include amino, lower alkylamino, e.g., methylamino, ethylamino; di(lower alkyl)amino, e.g., dimethylamino, diethylamino, dipropylamino; (hydroxy-lower alkyl)amino, e.g., β-hydroxyethylamino; di(hydroxy-lower alkyl)amino, e.g., di(hydroxyethyl)amino; phenyl(-lower alkyl)amino, e.g., benzylamino, and phenethylamino.

As indicated above, the nitrogen may join with the groups represented by $R^7$ and $R^8$ to form a 5 to 7 membered monocyclic heterocyclic containing, if desired, an oxygen, sulfur or an additional nitrogen atom, (not more than two hetero atoms altogether), that is, the two symbols $R^7$ and $R^8$ represent together tetramethylene, pentamethylene, hexamethylene, oxapentamethylene, oxatetramethylene, azahexamethylene, azapentamethylene, azatetramethylene, thiapentamethylene or thiatetramethylene. The heterocyclic group may also be substituted by one or two groups represented by $R^7$, $R^8$, $R^3$ and $R^4$.

Illustrative heterocyclic groups include piperidino, e.g., methylpiperidino, di(lower alkyl)piperidino, e.g., dimethylpiperidino, (lower alkoxy)piperidino, e.g., methoxypiperidino, pyrrolidino, (lower alkyl)pyrrolidino, e.g., 2-methylpyrrolidino, di(lower alkyl)pyrrolidino, e.g., 2,5-dimethylpyrrolidino, (lower alkoxy)pyrrolidino, e.g., ethoxypyrrolidino, morpholino, (lower alkyl)morpholino, e.g., 3-methylmorpholino or 2-methylmorpholino, di(lower alkyl)morpholino, e.g., 2,3-dimethylmorpholino, (lower alkoxy)morpholino, e.g., 2- or 3-ethoxymorpholino, thiamorpholino, (lower alkyl)thiamorpholino, e.g., 2-methylthiamorpholino or 2-methylthiamorpholino, di(lower alkyl)thiamorpholino, e.g., 2,3-diethylthiamorpholino or 2,3-dimethylthiamorpholino, (lower alkoxy)-thiamorpholino, e.g., 2-methoxythiamorpholino, piperazino, (lower alkyl)piperazino, e.g., 4-methylpiperazino, 2-methylpiperazino, di(lower alkyl)piperazino, e.g., 2,3-dimethylpiperazino, hydroxy-lower alkylpiperazino, e.g., 4-(2-hydroxyethyl)piperazino, hexamethyleneimino and homopiperazino.

Preferred are those compounds wherein $R^3$ and/or $R^4$ are chlorine, $R^1$ and $R^2$ are hydrogen, R is hydrogen or methyl, and $R^5$ is hydrogen, methyl or benzyl.

Examples of compounds falling within the present invention include, but are not limited to, the following:

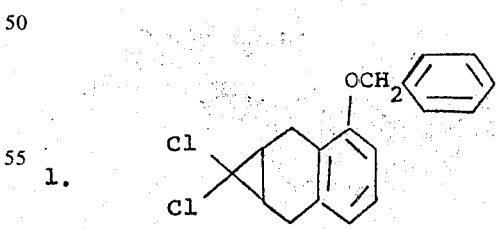

1.

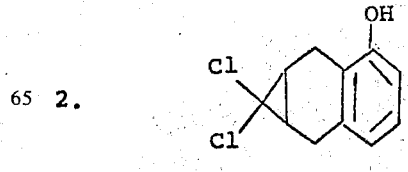

2.

3,969,392
3
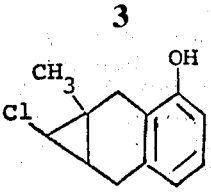
3.
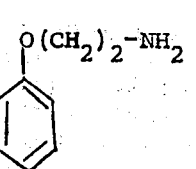
4.
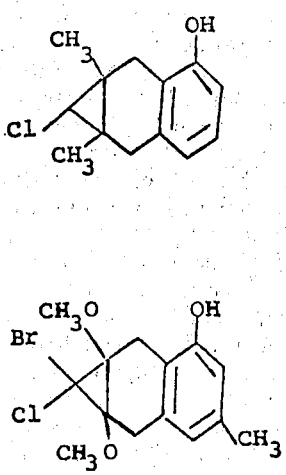
5.
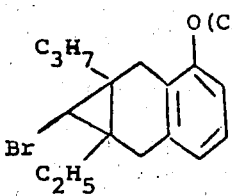
6.
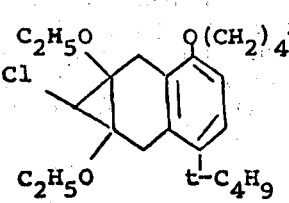
7.
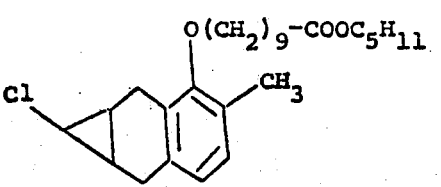
8.
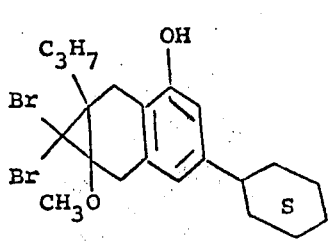
9.
4
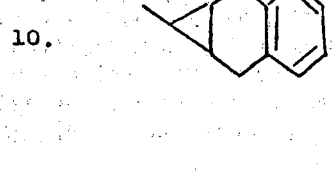
10.
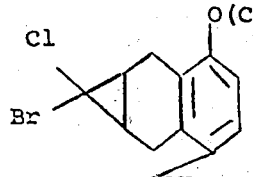
11.
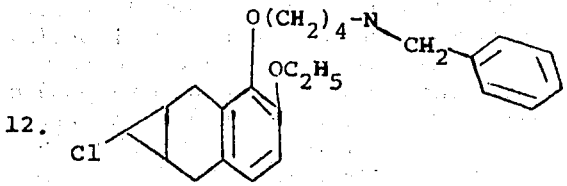
12.
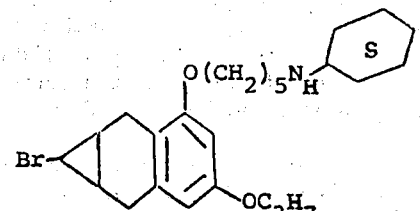
13.
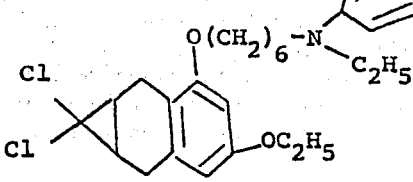
14.
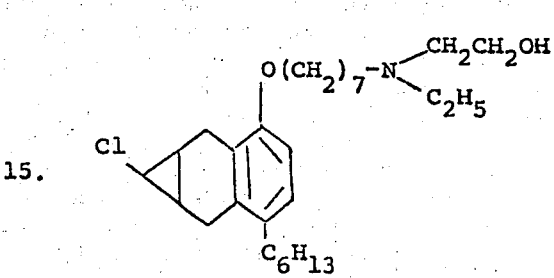
15.
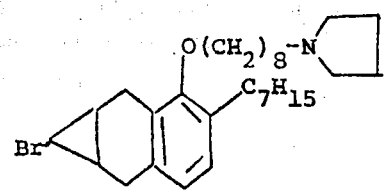
16.

17. [structure: Cl-substituted tricyclic with O(CH₂)₉-N-piperazine-NH and OC₅H₁₁]

18. [structure: Br, Cl-substituted tricyclic with O(CH₂)₃-N-thiomorpholine]

19. [structure: Cl-substituted tricyclic with O(CH₂)₄-N-morpholine]

20. [structure: Cl-substituted tricyclic with O(CH₂)₃-N-piperidine]

21. [structure: Br-substituted tricyclic with O(CH₂)₄-N-piperazine-N-CH₂CH₂OH]

Compounds of formula I can be prepared by the Birch reduction of a naphthol of the structure II [structure with $R^1$, OH, $R^2$, R]

i.e. by reducing the naphthol II with an alkali metal such as lithium or sodium, in a molar ratio of naphthol to alkali metal of within the range of from about 1:2 to about 1:50 and preferably from about 1:10 to about 1:20 in the presence of liquid ammonia, a proton source such as a lower alkanol, for example ethanol, and ethyl ether to give a 5,8-dihyronaphthol of the structure III [structure with $R^1$, OH, $R^2$, R]

The 5,8-dihydronaphthol is reacted with a halide of the structure $R^5X$ wherein $R^5$ is other than hydrogen and X is Cl, Br or I, in a molar ratio of naphthol to halide of within the range of from about 0.8:1 to about 1:1, in the presence of a base such as potassium carbonate, sodium ethoxide, sodium hydride or potassium-t-butoxide, at a temperature within the range of from about 65° to about 160°C, to form a compound of the structure V [structure with $R^1$, $OR^5$, $R^2$, R]

which is reacted with a halocarbene of the structure

VI :$CR^3R^4$ in a molar ratio of V:VI of within the range of from about 0.1:1 to about 1.5:1, at a temperature within the range of from about 0 to about 90°C, to form a compound of structure I.

As an alternate approach, a compound of formula V wherein $R^5$ is benzyl is first reacted with a halocarbene of structure :$CR^3R^4$ under the conditions specified above to give a compound of formula I where $R^5$ is benzyl i.e.

VII [structure with $R_3$, $R^1$, $R_4$, $R_2$, R, O-CH₂-phenyl]

The compound of formula VII is then debenzylated using 5-10% palladium/carbon as catalyst in a solvent like ethyl alcohol to give a compound of formula I wherein $R^5$ is H VIII [structure with $R_3$, $R^1$, $R_4$, $R_2$, R, OH]

The compound of formula VIII is then reacted with $R^5X$ ($R^5$ other than hydrogen) to give compound of general structure I.

The above alternate method is specially suited to the synthesis of materials wherein the $R^5$ substituent is sensitive to the conditions of the halocarbene addition step mentioned previously.

The solvents used for the above reactions may vary and include methyl and ethyl alcohols, tetrahydrofuran, dimethylformamide, benzene, toluene, dimethoxyethane, etc.

Examples of naphthol starting materials include the following:

1. 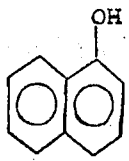

2. 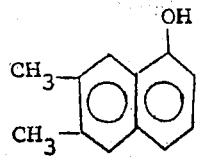

3. 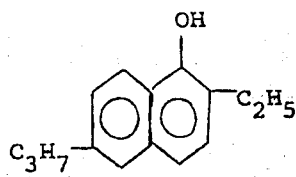

4. 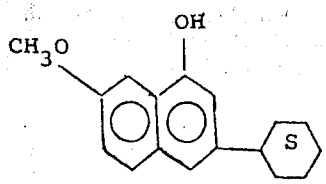

5. 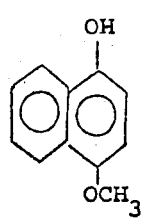

6. 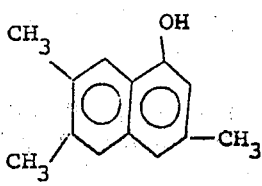

7. 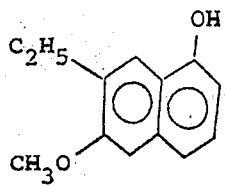

The halide $R^5X$ includes halides such as alkyl halides, for example methyl iodide, ethyl chloride, propyl bromide, benzyl chloride, as well as halides of the structure VII   $Hal-(CH_2)_m-\overset{O}{\overset{\|}{C}}OR^6$ such as

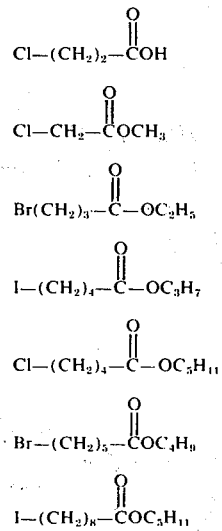

Examples of halides of the structure VIII

VIII   $Hal-(CH_2)_n-NR^7R^8$ suitable for use in preparing compounds of the invention include the following: dimethylaminoethyl chloride, dimethylaminopropyl chloride, methylethylaminomethyl bromide, ethyl-l-propylmlnobutyl iodide, methylaminoethyl chloride, aminopropyl bromide, methylbenzylaminopentyl chloride, cyclohexylaminoethyl bromide, hydroxyethylaminohexyl iodide, hydroxyethoxyethylaminopropyl chloride, pyrrolidinoethyl chloride, piperidinopropyl iodide, piperazinobutyl chloride, morpholinopentylbromide, thiamorpholinohexyl iodide as well as alkylene halides containing substituted heterocyclics as indicated hereinbefore.

Halocarbenes may be generated under basic conditions either by (a) reaction of a haloform or ethyltrihaloacetate with a base like potassium hydroxide or potassium-t-butoxide; or (b) reaction of a polyhalide with an alkyl lithium. Halocarbenes may be generated under non-basic conditions by the decomposition of phenylhalomethylmercury.

Compounds of formula I where $R_5$ is hydrogen may be conveniently prepared from compounds of formula I where $R_5$ is benzyl, by hydrogenolysis using palladium on charcoal or other known catalyst for reduction.

The compounds of formula I wherein the side chain has a basic amino function form physiologically acceptable acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Then any other salt may again be formed from the free base and the appropriate inorganic or organic acid. Illustrative are the hydrohalides, especially the hydrochloride and hydrobromide which are preferred, sulfate, nitrate, phosphate, oxalate, tartrate, maleate, fumarate, pamoate, citrate, succinate, benzoate, ascorbate, methanesulfonate, benzenesulfonate, toluenesulfonate, and the like.

The compounds of this invention can be utilized as parasiticides and rodenticides, being particularly useful against *Hymenolepis nana, Nematospiroides dubius, Nippostrongylus brasiliensis* and *Ascaris lumbricoides*. These compounds when utilized as parasiticides form the active ingredient in feed stuffs for cattle, hogs and chickens, being admixed with said feed stock in from 0.1 to 25 mg. per 100 kg weight of feed stuffs with the most preferred range being from about 5 to 10 mg. per kg. of feed stuffs.

As anti-inflammatory agents, the compounds of this invention may be used topically and/or orally in lieu of and in the same manner as cortisone in the treatment of acute inflammatory and allergic conditions of the eye, skin or mucose, e.g., as suspension, ointment or cream containing about 0.1 to about 2.5% by weight, of a compound of formula I or physiologically acceptable salt thereof. In the rabbit or cow, for example, a 1% ointment is applied to the skin area 3 to 4 times daily.

Furthermore, the new compounds of formula I are useful as antimicrobial agents and may be used to combat infections in animal species, such as mice, rats, dogs, guinea pigs and the like, due to organisms such as *Trichomonas vaginalis, Trichomonas foetus, Staphylococcus aureus, Salmonella schottmuelleri, Klebsiella pneumoniae, Proteus vulgaris, Escherichia coli, C. albicans* or *Trichophyton mentagrophytes*. For example, a compound or mixture of compounds of formula I or physiologically acceptable acid addition salts as defined hereinbefore may be administered orally to an infected animal, e.g., to a mouse, in an amount of about 5 to 25 mg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. They may also be applied topically, e.g., to dermatophytosis in a guinea pig, in a lotion, salve or cream at a concentration of about 0.01 to 3 percent by weight.

They may also be used as surface disinfectants. About 0.01 to 1 percent by weight of any of these substances may be dispersed on an inert solid or in a liquid such as water and applied as a dust or spray. They may be incorporated also, for example, in a soap or other cleansing agent, e.g., a solid or liquid detergent, detergent composition, for example, in general cleaning, in cleaning dairy barns or equipment or cleaning food handling or processing equipment.

The following examples are illustrative of the invention. All temperatures are on the centigrade scale.

EXAMPLE 1

3-(Benzyloxy)-1,1-dichloro-1a,2,7,7a-tetrahydro-1H-cyclopropa[b]naphthalene

A. 5,8-Dihydro-1-naphthol

A 3-l. three-necked flask, equipped with a dry ice condenser, a sealed Hershberg-type stirrer, and an inlet tube is set up in a hood and charged with 108g (0.75 mole) of 1-naphthol. The stirrer is started and to the rapidly stirred flask contents is added 1 l. of liquid ammonia as rapidly as possible (about 5 minutes). When the naphthol has gone into solution (about 10 minutes), 20.8g (3.0g atoms) of lithium metal is added in small pieces and at such a rate as to prevent the ammonia from refluxing too violently. After the addition of the lithium has been completed (about 45 minutes), the solution is stirred for an additional 20 minutes and is then treated with 170 ml (3.0 mole) of absolute ethanol which is added dropwise over a period of 30–45 minutes. The condenser is removed, stirring is continued, and the ammonia is evaporated in a stream of air introduced through the inlet tube. The residue is dissolved in 1 l. of water, and after the solution has been extracted with two 100 ml portions of ether, it is carefully acidified with concentrated hydrochloric acid. The product formed is taken into ether with three 250 ml extracts, and then the ether extract is washed with water and dried over anhydrous sodium sulfate. The ether is removed by evaporation to yield 106–108g (97–99%) of crude 5,8-dihydro-1-naphthol, mp 69°–71°. This material is dissolved in benzene, treated with charcoal, concentrated and crystallized to give pure 5,8-dihydro-1-naphthol, mp 70.5°–72°.

B. 5,8-Dihydro-1-naphthol, benzyl ether

Method (1) A mixture of 29.2g (0.2 mole) of 5,8-dihydro-1-naphthol, 28.0g (0.2 mole) of anhydrous $K_2CO_3$, 37.69g (0.22 mole) of benzyl bromide and 200 ml of dry acetone is stirred and refluxed for 12 hours. The solvent is removed in vacuo, the residue is mixed with 200 ml of water, and extracted with ether. The ether extract is washed with water, dried ($MgSO_4$) and evaporated to give 40g of oil, which solidifies on standing. A sample crystallized from pentane, melts at 69°–72°.

Anal. Calcd. for $C_{17}H_{16}O$: C, 86.40; H, 6.83.
Found: C, 86.55; H, 6.75.

Method (2) To a cooled solution of 21.9g (0.15 mole) of 5,8-dihydro-1-naphthol in 100 ml of anhydrous ethanol, 7.29g (0.15 mole) of 50% sodium hydride is added in portions. After the evolution of hydrogen has ceased, 25.6q (0.15 mole) of benzyl bromide is added dropwise, and the mixture refluxed with stirring for 12 hours. The solvent is removed in vacuo, the residue is mixed with 200 ml of water and extracted with chloroform. The chloroform extract is washed with water, dried ($MgSO_4$) and evaporated to give 33.5g (94%) of brown solid. It is dissolved in ether-pentane, decolorized with Darco, dried ($MgSO_4$) and evaporated to give 30g of product, identical to that obtained by Method (1).

C. 3-(Benzyloxy-1,1-dichloro1a,2,7,7a-tetrahydro-1H-cyclopropa [b]naphthalene

Method (1) A solution of 10g (0.042m) of benzyl ether of dihydro naphthol, in 150 ml of benzene and 11g of potassium t-butoxide are placed in a three-necked flask equipped with a $N_2$ inlet, dropping funnel and magnetic stirrer. The flask is cooled in an ice bath while 11.8g of $CHCl_3$ is added dropwise; the mixture turns dark. The temperature is maintained at about 25°. After the addition, the mixture is stirred ½ hour at room temperature. Then water is added to quench the reaction. The product is extracted with ether-benzene mixture, the organic extract is washed with water, dried ($MgSO_4$) and evaporated to give 13.8g of a dark oily solid. The solid is dissolved in MeOH, decolorized with Draco and filtered. On cooling 2.8g of crystals are obtained, mp 74–80°. Recrystallization from methanol gives yellow crystals, mp 82–85°, τ $CDCl_3$ singlet at 4.93τ (-$CH_2$ of benzyl), 2.58–3.4τ (aromatic protons).

Anal. Calcd. for $C_{18}H_{16}OCl_2$: C,67.73; H,5.06; Cl,22.22.

Found: C,67.78; H,5.24; Cl,22.13.

Method (2) To a solution of 2.3g (0.01 mole) of benzyl ether of dihydronaphthol in 300 ml of dry benzene, 3.9g (0.01 mole of phenyl (trichloromethyl)mercury is added, and the mixture refluxed for 48 hours. The precipitate (phenylmercuric chloride) is filtered off, and the solution concd. to give a solid residue. The solid is dissolved in methanol and allowed to crystallize slowly, 0.7g, mp 82°–85°, ir identical to the product obtained by Method (1).

EXAMPLE 2

1,1-Dichloro-1a,2,7,7a-tetrahydro-1H-cyclopropa[b]naphthalene-3-ol

A solution of 2g (0.006m) of product of Example 1 in 200 ml of 95% ethanol and a slurry of 1g of 10% Pd/C in 10 ml of 95% are placed in a Parr bottle and hydrogenated until the uptake of hydrogen ceases. The catalyst is filtered off, the solvent is evaporated in vacuo, $CHCl_3$ is added, dried ($MgSO_4$) and solvent evaporated in vacuo to give 1.3g (95%) of solid, mp 89°–93°C. Recrystallization from hexane gives crystals, mp 92.5°–96.5°, $\lambda_{nujol}^{max}$ 3450$cm^{-1}$ broad OH, τ$CDCl_3$ singlet at 5.25τ— OH, 2.8–3.6 — aromatic protons.

Anal. Calcd. for $C_{11}H_{10}OCl_2$: C,57.67; H,4.40; Cl,30.95. Found: C,57.72; H,4.47; Cl,30.73.

EXAMPLE 3

3-[2-(Dimethylamino)ethoxy]-1.1-dichloro-1a,2,7,7a-tetrahydro-1H-cyclopropa[b]naphthalene To a cooled solution of 2.3g (0.01 mole) of product of Example 2 in 50 ml of anhydrous ethanol 0.48g (0.01 mole) of 50% sodium hydride is added in portions. After the evolution of hydrogen has ceased, 1.5g (0.01 mole) of 2-(dimethylamino) ethyl bromide is added dropwise, and the mixture is refluxed with stirring for 3 hours. The solvent is removed in vacuo, the residue is mixed with 25 ml of water and the mixture extracted with chloroform. The chloroform extract is washed with water, dried ($MgSO_4$), and concd. to give 3-[2-(dimethylamino)ethoxy]-1,1-dichloro-1a, 2,7,7a-tetrahydro[1H]-cyclopropa[b]naphthalene.

EXAMPLES 4 to 21

In a manner similar to that described in Examples 1, 2 and 3, where the naphthol, halide ($R^5X$) and halocarbene employed are as shown in columns 1, 2 and 3 respectively, of Table I below, the product shown in Table IV is obtained.

TABLE I

| | Column 1 | | Column 2 | | Column 3 | | | Column 4 | |
|---|---|---|---|---|---|---|---|---|---|
| Examples | R | $R^1$ | $R^2$ | X | $R^5$ | $R^3$ | $R^4$ | R | $R^1R^2R^3R^4R^5$ |
| 4 | H | $CH_3$ | H | Cl | $C_2H_5$ | Br | Br | H | Same as in columns 1, 2 and 3 |
| 5 | H | $C_2H_5$ | $C_2H_5$ | Br | H | Br | Cl | H | |
| 6 | H | $OCH_3$ | H | I | $(CH_2)_3$ | Cl | H | H | |
| 7 | H | $OC_2H_5$ | H | Cl | $(CH_2)_2N(CH_3)(CH_3)$ | Cl | Cl | H | |
| 8 | 2-$C_3H_7$ | H | H | I | $CH_2CO_2C_2H_5$ | Br | H | 4-$C_3H_7$ | |
| 9 | 3-$C_2H_5$ | $CH_3$ | H | Br | $CH_3$ | Br | Br | 5-$C_2H_5$ | |
| 10 | 4-$OC_2H_5$ | H | H | Cl | $(CH_2)_3$-N◯N-$CH_3$ | Cl | Cl | 6-$OC_2H_5$ | |
| 11 | H | H | H | Cl | $(CH_2)_3$-N($C_2H_4OH$)($C_2H_4OH$) | Br | Br | H | |
| 12 | H | H | H | Cl | $CH_2CH_2CO_2H$ | Cl | Cl | H | Same as in columns 1, 2 and 3 |
| 13 | 2-⟨S⟩ | $C_4H_9$ | $C_4H_9$ | Br | $(CH_2)_2$-N⟨⟩ | Cl | Cl | 4-⟨S⟩ | |
| 14 | 3-⟨S⟩ | H | i-$C_3H_7$ | Cl | $CH_2$-⟨⟩ | H | Cl | 5-⟨⟩ | |
| 15 | 4-⟨S⟩ | $OC_4H_9$ | H | I | -$(CH_2)_3$-N($C_2H_5$)($CH_3$) | Br | Cl | 6-⟨S⟩ | |

TABLE I-continued

| Examples | Column 1 R | R¹ | R² | X | R⁵ | Column 3 R³ | R⁴ | R | Column 4 R¹R²R³R¹R⁵ |
|---|---|---|---|---|---|---|---|---|---|
| 16 | H | H | H | Cl | $-(CH_2)_3-N\bigcirc S$ | Cl | Br | H | |
| 17 | 2-$C_5H_{11}$ | $CH_3$ | $C_6H_{13}$ | Cl | $-(CH_2)_3-N\bigcirc O$ | Br | Cl | 4-$C_5H_{11}$ | |
| 18 | 3-$OC_5H_{11}$ | H | $C_7H_{15}$ | Br | $-(CH_2)_2-N\bigcirc$ | Br | Cl | 5-$OC_5H_{11}$ | |
| 19 | 4-$C_7H_{15}$ | $C_3H_7$ | $C_2H_5$ | Cl | $-(CH_2)_7-N\bigcirc NH$ | Cl | Cl | 6-$C_7H_5$ | |
| 20 | 2-$OC_2H_5$ | $OC_2H_5$ | $OC_2H_5$ | Br | $-(CH_2)_8-N\diagdown^{C_4H_9}_{C_3H_7}$ | Br | Cl | 4-$OC_2H_5$ | |
| 21 | H | H | H | I | $(CH_2)_4\overset{O}{\overset{\|}{C}}OC_4H_9$ | Cl | H | H | |

What is claimed is:
1. Compounds of the structure

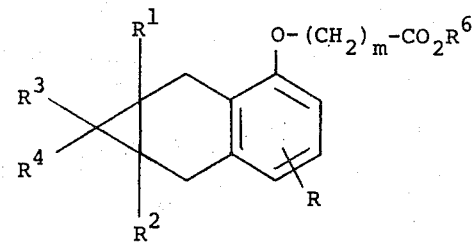

wherein R is hydrogen, lower alkyl, lower alkoxy or cycloalkyl having 3 to 6 carbon atoms; $R^1$ and $R^2$ are the same or different and are hydrogen, lower alkyl or lower alkoxy; $R^3$ and $R^4$ are the same or different and are hydrogen, chlorine or bromine, at least one of $R^3$ and $R^4$ being other than hydrogen; $R^6$ is hydrogen, lower alkyl or aralkyl; and $m$ is 1 to 10.

* * * * *

UNITED STATES PATENT AND TRADEMARK OFFICE
CERTIFICATE OF CORRECTION

PATENT NO. : 3,969,392

DATED : July 13, 1976

INVENTOR(S) : Venkatachala L. Narayanan

It is certified that error appears in the above-identified patent and that said Letters Patent are hereby corrected as shown below:

```
Column 1, line 12, "propanaphthalenes" should
      read --propa[b]naphthalenes--.
Column 6, line 3, "dihyronaphthol" should
      read --dihydronaphthol--.
Column 8, line 48, "ethyl-1-propylmlnobutyl" should
      read --ethyl-i-propylaminobutyl--.
Column 10, line 52, "25.6q" should read --25.6g--.
Column 10, line 62, "1-dichlorola," should read
      --1-dichloro-1a--.
Columns 11 and 12, Table I, under Column 2 please add:
```

$$R^5X$$

under Column 3 please add:

$$:CR^3R^4$$

Columns 13 and 14, Table I, under Column 2 please add:

$$R^5X$$

under Column 3, please add:

$$:CR^3R^4$$

Signed and Sealed this

Seventh Day of December 1976

[SEAL]

Attest:

RUTH C. MASON
*Attesting Officer*

C. MARSHALL DANN
*Commissioner of Patents and Trademarks*